United States Patent
Wong

(10) Patent No.: US 9,697,329 B2
(45) Date of Patent: Jul. 4, 2017

(54) SYSTEMS AND METHODS FOR IMPROVING THE PRIVACY-PROTECTION OF THE EXCHANGE OF STD TEST RESULTS AND THE UTILITY OF STD TEST RESULTS

(71) Applicant: Michael Wei-Chi Wong, John's Creek, GA (US)

(72) Inventor: Michael Wei-Chi Wong, John's Creek, GA (US)

( * ) Notice: Subject to any disclaimer, the term of this patent is extended or adjusted under 35 U.S.C. 154(b) by 127 days.

(21) Appl. No.: 14/821,860

(22) Filed: Aug. 10, 2015

(65) Prior Publication Data

US 2017/0046535 A1    Feb. 16, 2017

Related U.S. Application Data

(60) Provisional application No. 62/039,375, filed on Aug. 19, 2014, provisional application No. 62/181,775, filed on Jun. 19, 2015.

(51) Int. Cl.
| | |
|---|---|
| *G06F 19/00* | (2011.01) |
| *G06F 21/62* | (2013.01) |
| *G06Q 50/24* | (2012.01) |
| *G06Q 50/22* | (2012.01) |

(52) U.S. Cl.
CPC ........ *G06F 19/322* (2013.01); *G06F 21/6263* (2013.01); *G06Q 50/24* (2013.01); *G06F 19/324* (2013.01); *G06Q 50/22* (2013.01)

(58) Field of Classification Search
CPC .. G06F 21/6263; G06F 19/322; G06F 21/316; G06F 21/32; G06F 21/33; G06F 21/335; G06Q 50/00
USPC .......................................................... 726/30
See application file for complete search history.

(56) References Cited

U.S. PATENT DOCUMENTS

| | | | | |
|---|---|---|---|---|
| 6,272,481 | B1 * | 8/2001 | Lawrence ............... | G06N 5/025 706/10 |
| 6,551,243 | B2 * | 4/2003 | Bocionek ............... | A61B 5/411 128/923 |
| 2003/0225597 | A1 * | 12/2003 | Levine .................. | G06F 19/322 705/3 |
| 2005/0236474 | A1 * | 10/2005 | Onuma ................. | G06F 19/322 235/382 |
| 2006/0004588 | A1 * | 1/2006 | Ananda ............... | G06Q 20/3674 705/67 |
| 2006/0041450 | A1 * | 2/2006 | Dugan .................. | G06Q 50/22 705/2 |
| 2006/0277075 | A1 * | 12/2006 | Salwan ................. | G06F 19/322 705/3 |
| 2006/0277076 | A1 * | 12/2006 | Hasan .................. | G06F 19/322 705/3 |
| 2006/0282292 | A1 * | 12/2006 | Brink ................... | G06F 19/363 705/3 |
| 2008/0140449 | A1 * | 6/2008 | Hayes .................. | G06Q 10/10 705/2 |
| 2009/0307755 | A1 * | 12/2009 | Dvorak ................ | G06F 19/322 726/4 |
| 2010/0082371 | A1 * | 4/2010 | Kamp .................. | G06Q 10/06 705/3 |
| 2010/0131299 | A1 * | 5/2010 | Hasan .................. | G06F 19/322 705/3 |
| 2010/0318379 | A1 * | 12/2010 | Demopulos .......... | G06Q 10/10 705/3 |
| 2011/0225007 | A1 * | 9/2011 | Theis ................... | G06F 19/322 705/2 |
| 2013/0179193 | A1 * | 7/2013 | Perez ................... | G06Q 50/24 705/3 |
| 2014/0012601 | A1 * | 1/2014 | Gartner ............... | G06F 19/3443 705/3 |
| 2015/0106907 | A1 * | 4/2015 | Chawla ................ | G06Q 50/24 726/9 |
| 2015/0154357 | A1 * | 6/2015 | Biswas ................ | G06F 19/28 705/2 |
| 2015/0178449 | A1 * | 6/2015 | Ferry .................. | G06F 19/322 705/3 |

* cited by examiner

*Primary Examiner* — Hadi Armouche
*Assistant Examiner* — Shahriar Zarrineh

(57) ABSTRACT

Various aspects of the invention provide systems and methods for improving the privacy-protection of the exchange of STD's test results and the utility of STD test results. One aspect of the invention provides a computer-implemented method of improving privacy-protection during the exchange of STD test results by preventing the exchange of STD test results if user-definable criteria are not met and deliberately obscuring the cause of prevented attempts at exchanging STD test results. The method includes providing a software application for importing STD test results; inputting criteria; attempting to exchange STD test results; and either preventing or allowing the exchange of STD test results at a plurality of stages. Another aspect of the invention provides a computer-implemented method of improving the utility of STD test results by recommending safe sexual contact practices and sexual health-related products and services based upon the use of algorithms.

17 Claims, No Drawings

SYSTEMS AND METHODS FOR IMPROVING THE PRIVACY-PROTECTION OF THE EXCHANGE OF STD TEST RESULTS AND THE UTILITY OF STD TEST RESULTS

CROSS-REFERENCE TO RELATED APPLICATIONS

This application claims priority to U.S. Provisional Patent Application Ser. No. 62/039,375, filed Aug. 19, 2014, and U.S. Provisional Patent Application Ser. No. 62/181,775, filed Jun. 19, 2015. The entire contents of each application are hereby incorporated by reference herein.

TECHNICAL FIELD

The present invention relates generally to the use of STD test results and the exchange of STD test results, and more specifically, to improving the utility and privacy-protection of utilizing STD test results.

BACKGROUND

STD's pose a significant and growing health and economic problem. According to a 2013 report by the CDC using 2008 data, it is estimated that there are over 110 million STD infections among Americans, and 20 million Americans are newly infected each year, with an estimated 50% of these infections in persons between the age of 15-24. Prior to 1960, there were only two commonly transmitted STD's: syphilis and gonorrhea, both of which were easily treatable by antibiotics. Today, there are over thirty commonly transmitted STD's, with direct medical costs totaling over $16 billion USD in the United States.

Various approaches have been used to reduce the prevalence of STD's, either independently or in conjunction with one or more other approaches. For example, condoms are often used to reduce the possibility of STD transmission. However, according to some studies, they are far from being a reliable method of preventing STD transmission. In another example, medical treatment is often used to treat or cure STD's. However there are now many drug-resistant and incurable STD's, and many infected by STD's are unaware of their STD status. In another example, delayed-sex education is often used to reduce the incidence of sexual contact and thereby reduce the number of opportunities for the transmission of STD's. However, delayed-sex education will not prevent all people from having multiple sexual partners in their lifetimes. In another example, STD education is often used to allow people to be aware of the risks of sexual contact and symptoms of STD's to make better-informed decisions regarding sexual contact and obtaining medical treatment. However, sexual contact with someone not known to have the same sexual contact status will have some risk of STD transmission, and additionally, many STD's are either asymptomatic or show no obvious symptoms. In another example, STD testing is often used to allow people to make better-informed decisions regarding sexual contact and obtaining medical treatment. However, the exchange of STD test results can result in unnecessary disclosure of sensitive information and its successful use in making better-informed decisions regarding sexual contact requires personal knowledge of the specific STD's, and additionally, the usage of STD testing for obtaining medical treatment is so low that it is estimated that up to 90% of the 50-plus million Americans infected with genital herpes are unaware of their STD status. Despite the many existing approaches used to reduce the prevalence of STD's that are used today, they have proven unable to prevent STD's from becoming increasingly prevalent, year after year, for over half a century.

Accordingly, there is a need for new systems and methods to reduce the prevalence of STD's.

SUMMARY OF THE INVENTION

Various aspects of the invention provide systems and methods for improving the utility and privacy-protection of utilizing STD test results.

One aspect of the invention provides a system including a computing-device and software application for the one-way or multiple-way exchange of STD test results in a process which will: prevent the exchange of STD test results if users do not sufficiently meet user-definable criteria; obscure the causes for the prevention of the exchange of STD test results; allow users the option to manually verify other users' identities before allowing or denying the exchange of STD test results; and allow users the option to view how closely other users meet their own user-definable criteria and how closely they meet other user's criteria before allowing or denying the exchange of STD test results.

STD test results are inputted in accordance with HIPAA (Health Insurance Portability Accountability Act) guidelines. Criteria for allowing the exchange of STD test results can be inputted either by selecting presets or be user-defined.

To attempt the exchange of STD test results, one or more of the involved parties select the option to exchange STD test results, and then select another user to attempt to exchange STD test results. All involved parties must agree to the initialization of the exchange of STD test results for the process to continue further.

The exchange of STD test results may be prevented during the user verification or criterion comparison stage. No sensitive information will be disclosed if the exchange of STD test results is prevented at either of these stages.

If the minimum requirements for the exchange of STD test results are met, the percentage of criteria met by each and every user will be displayed to all involved parties, except the percentage of criteria met by a user in reference to himself as opposed to in reference to other users will only be disclosed to the user himself. After the match percentages are displayed, the involved parties may choose to allow or deny the exchange of STD test results. If the involved parties choose to deny the exchange of STD test results, the exchange of STD test results is prevented at this stage. If the involved parties choose to allow the exchange of STD test results, the STD-related information will be displayed. After STD test results are displayed, users will have the further option to exchange or display other information about themselves to others, such as STD-related criterion match percentage independent of non-STD-related match percentage, or criteria with regards to the users themselves such as physical characteristics and sexual preferences.

Another aspect of the invention provides a system including a computing-device and software application for improving the utility of STD test results by generating recommendations for safe sexual contact practices and sexual health products and services.

The variables used may be information inputted by the user, obtained from STD testing centers, or determined based upon other variables, such as the STD rates of a specific region. A few examples of the variables used in the algorithms are: STD test results of the user; STD test results of other users; STD-related criteria; user-inputted or algorithmically-estimated dates and activities of sexual contacts of users and non-users; user-inputted caution level of recommendations; user-inputted symptoms; statistical probability of false negatives of a specific STD test; and the risks, treatment methods, testing window, and window of transmissivity of STD's.

The times at which recommendations are provided will depend upon user application. A few examples of the times at which recommendations are provided is when users: view their own STD test results; exchange STD test results; have had sexual contact or may have had sexual contact with another user who has subsequently tested positive or negative for a specific STD at a time when the specific STD may have been transmissible; inputting symptoms that may be due to an STD; and viewing statistical probability of a user contracting specific STD's from sexual contact with a person from a specific region using user-estimated sexual contact history of said person.

The recommendations that are provided will be related to specific sexual health topics. A few examples of the recommendations that can be provided are: safe sexual contact practices and products to reduce the risks of transmitting known or possible STD's for a user; a user with other users; or a user with non-users; optimal dates, locations, and prices for STD testing; estimated odds of the user having contracted specific STD's without the user knowing; and products and services for the diagnosis of STD's.

DETAILED DESCRIPTION

Various aspects of the invention provide systems and methods for improving the utility and privacy-protection of utilizing STD test results.

One aspect of the invention provides a system including a computing-device, such as a cellular phone or computer, and software application for the one-way or multiple-way exchange of STD test results in a process which will: prevent the exchange of STD test results if users do not sufficiently meet user-definable criteria; obscure the causes for the prevention of the exchange of STD test results; allow users the option to manually verify other users' identities before allowing or denying the exchange of STD test results; and allow users the option to view how closely other users meet their own user-definable criteria and how closely they meet other user's criteria before allowing or denying the exchange of STD test results.

STD test results are inputted in accordance with HIPAA (Health Insurance Portability Accountability Act) guidelines. The user must fill out an HIPAA form authorizing the release of STD test results by one of the following means:
  At a medical or STD center.
  Electronically during registration for STD testing.
  Electronically by use of software implementing the aspect of the method of the invention.

Criteria for allowing the exchange of STD test results can be inputted either by selecting presets or be defined and according to user-definable settings for criteria. Criteria may be: STD-related; non-STD-related; with regards to the user himself for matching to other users' criteria; with regards to other users for matching to the user's criteria; user-definable keywords; and given custom statistical weight functions for calculating the percentage match of a user's STD test results and other criteria to other users'.

The algorithm used to generate the default STD-related criteria preset takes into consideration the user's STD test results to allow the user to be matched with other users with the same STD's or lack thereof. The default STD-related criteria preset is used as a template to generate presets to allow the user to be matched with other users with less STD's or more STD's than the user. The different permutations of presets will be made by allowing or disallowing specific STD's based upon their arbitrarily-defined "prevalence" on a scale of 1-5 and "undesirability of risking transmission" on a scale of 1-5, so that a total of 26 different presets will be generated.

The "prevalence" of an STD is based upon the estimated percentage of sexually-active people in a default or user-defined location and radius who have the specific STD falling within an arbitrarily-defined range of percentages, such as 1-2%, 3-6%, 7-15%, 16-25%, and 26%+.

The "undesirability of risking transmission" of an STD is based upon factors such as symptoms, treatment cost, curability, transmission odds, odds of developing drug-resistance, etc.

Some examples of STD-related criteria are:
  Specific STD's (family or strain-specific) of the user according to STD test results.
  Specific STD's of other users according to STD test results known or suspected of having had sexual contact with the user as inputted by the user or other users.
  Conservative odds of a user being infected by specific STD's without STD test results showing that he tests positive for said specific STD's.
  Conservative odds of a user still being infected by specific STD's after taking medication for said STD's.
  Gender.
  Age.
  Sexual preferences.
  Sexual activity preferences.
  Sexual health products for reducing the odds of STD transmission that the user is willing to use.
  Sexual contact history according to the user.
  Sexual contact history regarding the user according to other users.
  "Veracity rating" of the user.
  Sexual contact history estimate based upon the "veracity rating" of the user.
  User-estimated risk level of other users or non-users.
  Regional STD rates of a default or user-defined region or radius.
  Estimated odds of STD infection based upon user-inputted symptoms or lack thereof.
  User-definable keywords such as specific STD's or sexual activities preferences which are not already displayed as criterion options by the software.

The user has the option to manually input user-definable criteria and minimum requirements for the exchange of STD test results to occur. The options may consist of one or more of the following, in no specific order, and at the option of the user:
  selecting presets for STD-related criteria and minimum requirements for the exchange of STD test results to occur for use as a template for manually-inputting user-definable criteria and minimum requirements for the exchange of STD test results to occur;
  customizing STD-related and non-STD-related criteria, criterion weight functions, and minimum requirement for the exchange of STD test results to occur as a percentage;
    of which the criteria may be default, selected by user, or created as keywords;

of which the criterion weight functions may:
  apply to criterion in reference to other users;
  apply to other users' criteria in reference to the user himself; and
  add to the percentage of criteria met depending upon whether a criterion is either met, not met, or not specified by the user; and
of which the minimum requirement is:
  default or selected by a user;
  the minimum percentage of criteria met for the exchange of STD test results to occur after adjusting for criterion weight functions;
  the maximum percentage of criteria allowed to be met by the user himself for the exchange of STD test results to occur after adjusting for criterion weight functions if criteria in reference to himself are used; and
  either a default or user-defined fraction of the maximum possible percentage of criteria met.

Some STD-related criteria are algorithmically-determined and may be highly-dependent upon statistical data and/or arbitrarily-defined information. Some criteria will be described in more detail for the purpose of giving examples of the methods by which variables are determined and what types of algorithms are used in the invention. Different algorithms will have different requirements for variables to be determined before the algorithms may be utilized. Variables will have arbitrarily-defined variable weight functions for the purpose of displaying to the user the percentage of variables which have already been determined, the percentage of variables required to be determined for the algorithms to be utilized, and the maximum percentage of determinable variables for the algorithms. Users will be unable to utilize the algorithms until the minimum requirements are met, and they will be displayed with the current percentage of determined variables as a ratio of the minimum requirement of variables determined for the algorithms to be utilized and as a ratio of the maximum percentage of determinable variables of the algorithms.

The criterion of conservative odds of a user being infected by specific STD's without STD test results showing that he tests positive for said specific STD's requires the use of individual algorithms for each specific STD. The algorithm of such a criterion weighs variables differently depending upon the specific STD the algorithm is made for and some examples of the variables taken into consideration are:
  Specific STD's (family or strain-specific) of the user according to STD test results.
  Specific STD's of other users according to STD test results known or suspected of having had sexual contact with the user as inputted by the user or other users.
  Specific STD's of other users according to STD test results.
  Statistical odds of false negatives of the utilized STD test methodology in the most recent STD test of a specific STD.
  Date since the STD was last tested for.
  Incubation period of the STD.
  Testing window of the STD.
  Self-diagnosable symptoms of the STD.
  Windows of when self-diagnosable symptoms of the STD become visible.
  Sexual contact history with other users or non-users at dates where if the STD was transmitted to the user, the STD would not have been tested during the appropriate testing window, as inputted by the user and other users who have claimed to have had sexual contact with the user at dates where if the STD was transmitted to the user, the STD would not have been tested during the appropriate testing window.
  Sexual contact history estimate based upon the "veracity rating" of the user.
  Sexual contact preferences of the user and of other users and non-users who may have had sexual contact with the user at dates where if the STD was transmitted to the user, the STD would not have been tested during the appropriate testing window, as inputted by the user or other users.
  Conservative statistical odds of the users and non-users who may have had sexual contact with the user at dates where if the STD was transmitted to the user, the STD would not have been tested during the appropriate testing window.
  Conservative statistical odds of the STD being transmitted to the user given the sexual contact preferences of the user and of other users and non-users who may have had sexual contact with the user at dates where if the STD was transmitted to the user, the STD would not have been tested during the appropriate testing window.
  User-inputted symptoms or lack thereof into the software when attempting self-diagnosis of STD's or when prompted by the software to input whether specific symptoms are apparent during a window of discernibility of self-diagnosable symptoms of the STD.

The criterion of conservative odds of a user still being infected by specific curable STD's or having a specific STD in an infectious state after taking medication for said STD's requires the use of individual algorithms for each specific STD. The algorithm of such a criterion weighs variables differently depending upon the specific STD the algorithm is made for and takes into consideration all of the variables taken into consideration by the algorithms used for the criterion of conservative odds of a user being infected by specific STD's without STD test results showing that he tests positive for said specific STD's and some examples of the variables taken into consideration are:
  Medication being used by the user, as manually-inputted by the user or automatically-obtained from the provider of the medication with permission of the user in accordance to HIPAA guidelines.
  Conservative estimate of the efficacy of the medication in either curing a specific STD or preventing a specific STD from being in an infectious state at different periods of duration, frequencies, lapses, and/or quantities of medication used.
  Duration, frequency, lapses, and/or quantity of medication used as inputted by the user.
  Self-diagnosable symptoms of a specific STD.
  Conservative estimate of the odds of the user still being infected by specific STD's or being in an infectious state of the STD given the user inputted duration, frequency, lapses, and/or quantity of medication used.
  Estimated odds of the duration, frequency, lapses, and/or quantity of medication used as inputted by the user being accurate based upon the "veracity rating" of the user.

The criterion of gender may be used as a response to the non-STD-related criterion of sexual preference, and it may be used as a variable for refining the accuracy of the output of STD-related algorithms, which requires the use of individual algorithms for different genders to calculate. The algorithm of such a criterion weighs variables differently depending upon the different arbitrarily-defined estimated odds of having contracted, contracting, transmitting, false positives during specific STD testing methodology of, false negatives during specific STD testing methodology of, or displaying self-diagnosable symptoms of specific STD's for different genders. In example, an STD may be significantly more transmissible from a particular gender than other genders, have different incubation periods, have different testing windows, have different symptoms, have different preferred testing methodologies, and the different testing methodologies may have different odds of false positives or false negatives.

The criterion of age may be used as a response to the non-STD-related criterion of age preference, and it may be used as a variable for refining the accuracy of the output of STD-related algorithms, which requires the use of individual algorithms for different ages to calculate. The algorithm of such a criterion weighs variables different depending upon the arbitrarily-defined estimated odds of having contracted, contracting, transmitting, false positives during specific STD testing methodology of, false negatives during specific STD testing methodology of, or displaying self-diagnosable symptoms of specific STD's for different ages. In example, physiological changes to a female's genitalia as the female ages allows her to become progressively less susceptible to certain types of STD's. In another example, different age groups may have significantly different STD rates.

Some examples of the variables used in the algorithm for determining the criterion of sexual health products for reducing the odds of STD transmission that the user is willing to use are:
  The criterion of conservative odds of a user being infected by specific STD's without STD test results showing that he tests positive for said specific STD's.
  The criterion of conservative odds of a user still being infected by specific curable STD's or having a specific STD in an infectious state after taking medication for said STD's.
  Each specific products the user is willing to use as inputted by the user and by other users in regards to the user.
  Willingness of the user to use each specific product as inputted by the user and by other users in regards to the user on a scale of 1-10.
  Proper or improper use of each specific product as inputted by the user and by other users in regards to the user on a scale of 1-10.
  Ownership of each specific product by the user as inputted by the user, other users, or automatically-obtained from the provider of each specific product with permission of the user.
  Conservative statistical odds of the efficacy of each specific product to successfully prevent the transmission of specific STD's when used properly or improperly on a scale of 1-10.

Some examples of the variables used in the algorithm for determining the criterion of sexual contact history as inputted by the user are:
  Instances of sexual contact with other users or non-users as inputted by the user.
  Sexual activities and their durations in each instance as inputted by the user.
  Sexual health products for reducing the odds of STD transmission used in each instance as inputted by the user.
  How properly or improperly specific sexual health products for reducing the odds of STD transmission were used in each instance on a scale of 1-10 as inputted by the user.
  User-inputted gender and/or age of other non-users he has had sexual contact with.
  User-inputted estimated risk level of other users or non-users he has had sexual contact with on a scale of 1-10.

The criterion of sexual contact history regarding the user according to other users utilizes an algorithm that takes into consideration the same variables as used in the algorithm utilized in the criterion of sexual contact history as inputted by the user as prior described, but instead utilizes information inputted by the other users in regards to the user instead of information inputted by the user.

Some examples of the variables used in the algorithm for determining the criterion of "veracity rating" of the user are:
  Frequency of testing of specific STD's.
  Conservative estimate of the reliability of STD test results, i.e. if from an STD center following HIPAA guidelines, if from a reputable or disreputable STD center, and/or if utilizing STD testing methods with low false positive and/or low false negative rates.
  How closely user-inputted duration, frequency, lapses, and/or quantity of medication matches the recommendation duration, frequency, and/or quantity of medication recommended for curing or treating specific STD's of the user.
  User-inputted sexual contact history with other users and non-users.
  How closely current STD test results where the user tests positive for specific STD's of the user reflects the conservative odds of the user having contracted the STD's he tests positive for after taking into consideration the:
    Statistical odds of false positives of the utilized STD test for each specific STD the user tests positive for.
    User-inputted sexual contact history with other users and non-users.
    Statistical odds of sexually-active people in the region having each specific STD the user tests positive for after taking into consideration the user-inputted gender and/or age of non-users the user has had sexual contact.
  Percentage of input of sexual contact history information in agreement between the user and other users, with different input having arbitrarily-defined input weight functions.
  Percentage of input of sexual contact history information in disagreement between the user and other users, with different input having arbitrarily-defined input weight functions.

Some examples of the variables used in the algorithm for determining the criterion of sexual contact history estimate based upon the "veracity rating" of the user are:
  Sexual contact history as inputted by the user.
  Sexual contact history as inputted by other users in regards to the user.
  "Veracity rating" of the user.
  "Veracity rating" of other users.
  Estimated odds of what sexual contact history information is accurate or inaccurate based upon what inputted information is in agreement by different users and the "veracity rating" of the users.

Some examples of the variables used in the algorithm for determining the criterion of user-estimated risk level of other users or non-users are:
  User-estimated risk level of other users or non-users on a scale of 1-10.
  Regional STD rates.

Sexual contact activities as inputted by the user, or if not inputted by the user, extrapolated from user input regarding sexual contact activities and/or preferences.

If applicable, the sexual contact activities preferences of other users.

Some examples of the variables used in the algorithm for determining the criterion of regional STD rates of a default or user-defined region or radius are:

Statistical data regarding the STD rates of different regions.

Conservative estimates of the STD rates of different regions.

Conservative estimates of the STD rates of different regions given specific gender and age combinations according to user-inputted information or extrapolated from user input regarding the STD-related criterion of gender and the non-STD-related criteria of age.

Averaged conservative estimates of different regional STD rates when a radius is specified encompassing two or more regions, with conservative estimates of different regional STD rates being given different weight functions in proportion to the percentage of area they occupy of said specified radius.

Averaged conservative estimates of different regional STD rates given specific gender and age combinations when a radius is specified encompassing two or more regions, with conservative estimates of different regional STD rates being given different weight functions in proportion to the percentage of area they occupy of said specified radius.

The criterion of estimated odds of STD infection based upon user-inputted symptoms or lack thereof requires the use of individual algorithms for each specific STD. The algorithm of such a criterion weighs variables differently depending upon the specific STD the algorithm is made for and some examples of the variables taken into consideration are:

Sexual contact history as inputted by the user and other users.

Conservative estimates of specific STD's exhibiting or not exhibiting specific self-diagnosable symptoms at specific windows of symptom discernibility.

Conservative estimates of false positive or false negative of self-diagnosis of each user-inputted symptom.

User-inputted symptoms, including specific regions of symptoms, when the user attempts to self-diagnose with the assistance of the software.

User-inputted symptoms or lack thereof when prompted by the software to attempt to find specific self-diagnosable symptoms of STD's which the software has determined the user has exceeded arbitrarily-defined or user-defined thresholds of estimated odds of having contracted.

User-inputted symptoms or lack thereof when prompted by the software to attempt to find specific self-diagnosable symptoms of STD's which are arbitrarily-defined to be prudent to attempt to find after the user has inputted specific symptoms or lack thereof.

User-inputted estimated confidence level of each user-inputted symptom.

STD-related criteria and non-STD-related criteria may be in reference to other users with regards to the user's criteria for those users, or they may be in reference to the user himself with regards to other users' criteria for the user. In examples of criteria in reference to other users with regards to the user's criteria for those users, there may be criteria that a user requires other users to meet for the exchange of STD test results to occur, and there may be criteria that other users require other users to meet for the exchange of STD test results to occur. In an example of criteria in reference to the user himself with regards to other users' criteria for the user, there may be criteria that a user specify should not or must not be used by other users with regards to the user himself without the exchange of STD test results being prevented or the percentage of criteria reduced as a result, such as if the other user specifies that if other users have HIV that the attempt to exchange STD test results will not be prevented or the percentage of criteria met will only be reduced. Criteria in reference to other users and in reference to the user himself may be used independently or in conjunction with each other, according to default settings or according to user-defined settings.

STD-related criteria and non-STD-related criteria will have criterion weight functions associated to each of them individually. The criterion weight functions may be default or user-defined. The criterion weight functions may add to, subtract from, or not affect the percentage of criteria met for the purpose of determining whether or not the minimum requirements for the exchange of STD test results have been met. Whether or not the criterion weight functions of specific criteria will add to, subtract from, or not affect the percentage of criteria met depends upon whether the user to which the specific criteria apply:

Meets each specific criteria.

Does not meet each specific criteria.

Or has not inputted information for each specific criterion.

The minimum requirement for the exchange of STD test results are the minimum percentages of criteria required to be met for the exchange of STD test results to occur after adjusting for criterion weight functions. The minimum percentage of criteria required to be met is default or user-definable, and will be displayed as a ratio of the maximum possible percentage of criteria if all criteria were to be met. The minimum percentages of criteria required to be met may apply to the combined average of percentages of STD-related criteria and non-STD-related criteria met as in default or may apply to the separate percentage of STD-related criteria met and to the separate percentage of non-STD-related criteria met if so defined by the user. If separate minimum percentages of STD-related criteria and non-STD-related criteria to be met are used, their minimum percentages may be independently changed according to user-defined settings. The percentages of criteria met will not be displayed if one or more parties attempting to exchange STD test results does not meet the minimum requirements for the exchange of STD test results to occur. If the percentages of criteria met are displayed, they will be displayed as a ratio of the maximum possible percentage of criteria met if all criteria were to be met. As with criteria and criterion weight functions, minimum requirements for the exchange of STD test results to occur may be in reference to other users or in reference to the user himself as defined by default or user-defined settings.

To attempt the exchange of STD test results, one or more of the involved parties select the option to exchange STD test results, and then select another user to attempt to exchange STD test results. All involved parties must agree to the initialization of the exchange of STD test results within the default or user-defined time limit for the process to continue further.

The following types of STD test results exchanges can be performed:

One-way exchange, where an individual user attempts to exchange STD test results to an establishment user, i.e. entry to an HIV club.

Two-way exchange, where two individual users attempt to exchange their STD test results with each other, i.e. two people wanting to see each others' STD test results before considering sexual contact with each other.

Simultaneous two-way exchange, where an individual user attempts to exchange STD test results with multiple individual users separately, i.e. online matchmaking.

Multiple-way, where three or more individual users attempt to exchange their STD test results with each other.

Selection of other users may be made through many possible means such as: inputting phone number, e-mail address, username, one-time use alphanumeric code or link, Wi-Fi, Bluetooth, matchmaking profile, phone-to-phone tapping, etc. Selection may be made through many possible devices, such as cellular phones, computers, devices designed specifically for the electronic exchange of STD test results, or landline phones after generating unique hashtag phone codes and auditory and/or code input user verification for individual users.

The software should be cross-platform and may be either standalone or integrated into other software. The software should be cross-platform so that users may be able to attempt the exchange of STD test results regardless of whether they utilize the Android cellular phone software platform, the Apple iOS cellular phone software platform, Windows computer operating system, or Mac operating system. The software can be offered as both standalone software or as an integrated component of other software, so that users may attempt to exchange STD test results through a plurality of software such as sexual health-related cellular phone app, sexual health-related desktop/laptop software, back-end server hosted software designed for facilitating landline phone-based exchange of STD test results, sexual health-related website, matchmaking or dating website integrated applet, e-mail integrated applet, or social media integrated applet.

If all involved parties have agreed to initialize the exchange of STD test results, any required user verification information will need to be inputted if not already-inputted unless no user verification information is required by any users. If any of the default or user-definable user verification methods are not met by one or more involved parties, the involved parties will only be displayed with the text: "Insufficient user verification information" and the exchange of STD test results will be prevented. If any of the user verification methods have failed, the involved parties will only be displayed with the text: "User verification failed" and the exchange of STD test results will be prevented. No sensitive information such as STD test results, STD-related and non-STD-related criteria, criterion weighting, or percentages of criteria met will be disclosed if the exchange of STD test results is prevented at these stage.

User verification information may be automatically-verifiable or manually-verifiable. User verification information may be obtained by the user or other users, or by the user's computing-device or by other users' computing-device. In example, a user may require that an attempt to exchange STD test results may not proceed beyond this stage unless the user is able to take one or more images of other involved parties with the user's own computing-device, and the images transferred to and processed by a back-end server, for the purpose of confirming the identities of the other involved parties via facial and fingerprint recognition. Multiple user-verification processes may be used according to default or user-defined settings. User verification methods required to be used for the exchange of STD test results may be default or user-defined. The allowable duration of time for the input of user verification information may be default or user-defined. Different devices operating different software implementing the methods of the invention will be able to support different user verification methods.

Some examples of automatically-verifiable user verification methods are:

Facial recognition.

IR recognition.

Fingerprint recognition.

Voice recognition.

OCR-based driver's license, credit card, and/or STD test results recognition.

Alphanumeric password.

Gestural password.

Auditory password.

Some examples of manually-verifiable user verification methods are:

Name, address, age, gender, other personal information, and/or driver's license of a user photocopied during STD testing, the electronic images of which other users can be furnished with on their own devices for comparison to the user's physical appearance in real life, the user's real driver's license, or other proofs of identity such as credit card.

Audio sample of the user's name, age, gender, other personal information, or standardized text audio sample said by either the user himself, a voice synthesizer, or real voice of another person, furnished by a back-end computing-device to other users on their own devices when they call an authorized phone number and input the user's unique hashtag code generated when registering for software implementing the methods of the invention.

If user verification requirements are met and user verification processes are successful, the software will proceed to then determine if all involved parties meet the default or user-defined minimum criterion percentages required for the exchange of STD test results to occur. If any of the user-definable minimum requirements for the exchange of STD test results to occur are not met, the involved parties will only be displayed with the text: "Not a match" and the exchange of STD test results will be prevented. If the minimum requirements are met, the percentage of criteria met by each and every user will be displayed to all involved parties, except the percentage of criteria met by a user in reference to himself as opposed to in reference to other users will only be disclosed to the user himself. After the match percentages are displayed, the involved parties may choose to allow or deny the exchange of STD test results. If the involved parties choose to deny the exchange of STD test results, the exchange of STD test results is prevented at this stage. The only sensitive information that will be disclosed is the percentages of criteria met if the exchange of STD test results is prevented at this stage.

If the involved parties choose to allow the exchange of STD test results, the STD-related information will be displayed. After STD test results are displayed, users will have the further option to agree to share up-to-date STD test results with each other or exchange or display other information about themselves to others, such as STD-related criterion match percentage independent of non-STD-related match percentage, or criteria with regards to the users themselves such as the users' own physical characteristics and sexual preferences.

If the user has automatically or manually agreed to share up-to-date STD test results with one or more other users, the user may define the requirements for updating those users she has exchanged STD test results with by selecting whether:
- other users she has exchanged STD test results with will be allowed to be updated with her most current STD test results as they become available;
- said updating of STD test results must be reciprocated for the exchange of STD test results to occur or to continue; and
- said updating will cease if any involved parties chooses to cancel said updating.

Another aspect of the invention provides a system including a computing-device and software application for improving the utility of STD test results by generating recommendations for safe sexual contact practices and sexual health products and services.

Many of the same variables, criteria, computing-devices, user verification methods, and times and circumstances under which the two methods of the invention may be used are the same and should be assumed to apply to either aspect of the invention when described for either aspect when applicable. It is intended for both methods to be used in conjunction with each other for optimal function of both.

The variables used may be information inputted by the user, obtained from STD testing centers, or determined based upon other variables, such as the STD rates of a specific region. A few examples of the variables used in the algorithms are: STD test results of the user; STD test results of other users; STD-related criteria; user-inputted or algorithmically-estimated dates and activities of sexual contacts of users and non-users; user-inputted conservativeness level of recommendations; user-inputted symptoms; statistical probability of false negatives of a specific STD test; and the risks, treatment methods, testing window, and window of transmissivity of STD's.

The times at which recommendations are provided will depend upon user application. A few examples of the times and circumstances under which recommendations may be provided is when users: view their own STD test results; exchange STD test results; have had sexual contact or may have had sexual contact with another user who has subsequently tested positive or negative for a specific STD at a time when the specific STD may have been transmissible; inputting symptoms that may be due to an STD; and viewing statistical probability of a user contracting specific STD's from sexual contact with a person from a specific region using user-estimated sexual contact history of said person.

The recommendations that are provided will be related to specific sexual health topics. Some recommendations that can be provided are:
- Safe sexual contact practices and products to reduce the risks of transmitting known or possible STD's for a user in general; a user with other users; or a user with non-users.
- Optimal dates, locations, and prices for the most suitable STD tests.
- Estimated odds of the user having contracted specific STD's without the user knowing.
- Products and services for the diagnosis, treatment, or cure of STD's.

The recommendation of safe sexual contact practices and products to reduce the risks of transmitting known or possible STD's for a user in general is generated by use of an algorithm that takes into consideration at least the following variables:
- Specific STD's (family or strain-specific) of the user according to STD test results.
- Specific STD's of other users according to STD test results known or suspected of having had sexual contact with the user as inputted by the user or other users.
- Conservative odds of a user being infected by specific STD's without STD test results showing that he tests positive for said specific STD's.
- Conservative odds of a user still being infected by specific STD's after taking medication for said STD's.
- Gender.
- Sexual preferences.
- Sexual activity preferences.
- Sexual health products for reducing the odds of STD transmission that the user is willing to use.
- Sexual contact history according to the user.
- Sexual contact history regarding the user according to other users.
- "Veracity rating" of the user.
- Sexual contact history estimate based upon the "veracity rating" of the user.
- User-estimated risk level of other users or non-users.
- Regional STD rates of a default or user-defined region or radius.
- Estimated odds of STD infection based upon user-inputted symptoms or lack thereof.

Different sexual contact activities have different statistical odds of transmitting STD's. By avoiding sexual contact activities based upon known or suspected STD's and/or known or suspected regions of STD transmissivity, the statistical odds of transmitting STD's can be reduced or eliminated. Some STD's are able to be infectious from regions other than the mucous membranes (genitals, mouth, eyes, etc.), such as the skin, so that users should be able to specify possibly applicable infectious regions of the body. Some examples of the variables used in the algorithm for generating the recommendation of safe sexual contact practices to reduce the risk of transmitting known or possible STD's for a user in general is generated by use of an algorithm that takes into consideration at least the following variables:
- The criterion of conservative odds of a user being infected by specific STD's without STD test results showing that he tests positive for said specific STD's.
- The criterion of conservative odds of a user still being infected by specific curable STD's or having a specific STD in an infectious state after taking medication for said STD's.
- Gender.
- Sexual preferences.
- Sexual activity preferences.
- Sexual contact history according to the user and other users.
- "Veracity rating" of the user.
- Sexual contact history estimate based upon the "veracity rating" of the user.
- User-estimated risk level of other users or non-users.
- Regional STD rates of a default or user-defined region or radius.
- Estimated odds of specific regions of a user being regions of transmissivity of specific STD's.
- Estimated odds of transmitting specific STD's from specific regions of the user if those regions are regions of transmissivity of specific STD's.

Each safe sexual contact practice the user is willing to use as inputted by the user and by other users in regards to the user.

Willingness of the user to use each specific practice as inputted by the user and by other users in regards to the user on a scale of 1-10.

Proper or improper use of each specific practice as inputted by the user and by other users in regards to the user on a scale of 1-10.

Statistical odds of the efficacy of each specific practice to successfully prevent the transmission of specific STD's when used properly or improperly on a scale of 1-10.

The algorithm for generating the recommendations of safe sexual contact practices to reduce the risk of transmitting known or possible STD's with other users takes into consideration at least all of the variables taken into consideration in the algorithm for the same with regards to the user in general, while also taking into consideration at least the:

Algorithm for the same with regards to other users.
User-estimated risk level of other users.

The algorithm for generating the recommendations of safe sexual contact practices to reduce the risk of transmitting known or possible STD's with non-users takes into consideration at least all of the variables taken into consideration in the algorithm for the same with regards to the user in general, while also taking into consideration at least the:

Regional STD rates of a default or user-defined region or radius.

User-estimated risk level of other users or non-users.

Some examples of the variables used in the algorithm for generating the recommendation of products to reduce the risk of transmitting known or possible STD's for a user in general is generated by use of an algorithm that takes into consideration at least the following variables:

The criterion of conservative odds of a user being infected by specific STD's without STD test results showing that he tests positive for said specific STD's.

The criterion of conservative odds of a user still being infected by specific curable STD's or having a specific STD in an infectious state after taking medication for said STD's.

Gender.
Sexual preferences.
Sexual activity preferences.
Sexual contact history according to the user and other users.
"Veracity rating" of the user.
Sexual contact history estimate based upon the "veracity rating" of the user.
User-estimated risk level of other users or non-users.
Regional STD rates of a default or user-defined region or radius.
Estimated odds of specific regions of a user being regions of transmissivity of specific STD's.
Estimated odds of transmitting specific STD's from specific regions if those regions are regions of transmissivity of specific STD's.
Each product the user is willing to use as inputted by the user and by other users in regards to the user.
Willingness of the user to use each specific product as inputted by the user and by other users in regards to the user on a scale of 1-10.
Proper or improper use of each specific product as inputted by the user and by other users in regards to the user on a scale of 1-10.
Statistical odds of the efficacy of each specific product in different specific regions to successfully prevent the transmission of specific STD's when used properly or improperly on a scale of 1-10.

The algorithm for generating the recommendations of products to reduce the risk of transmitting known or possible STD's with other users takes into consideration at least all of the variables taken into consideration in the algorithm for the same with regards to the user in general, while also taking into consideration at least the:

Algorithm for the same with regards to other users.
User-estimated risk level of other users.

The algorithm for generating the recommendations of products to reduce the risk of transmitting known or possible STD's with non-users takes into consideration at least all of the variables taken into consideration in the algorithm for the same with regards to the user in general, while also taking into consideration at least the:

Regional STD rates of a default or user-defined region or radius.

User-estimated risk level of other users or non-users.

The recommendation for optimal dates, locations, and prices for STD testing is generated by using an algorithm that takes into consideration at least the following variables:

The criterion of conservative odds of a user being infected by specific STD's without STD test results showing that he tests positive for said specific STD's.

The criterion of conservative odds of a user still being infected by specific curable STD's or having a specific STD in an infectious state after taking medication for said STD's.

"Veracity rating" of the user.
Default or user-defined region or radius for finding physical STD centers.
Prices of the most suitable STD testing methodologies.
Reputability of STD centers within regions or radius.
Distance of STD centers within regions or radius from the user.

EQUIVALENTS

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., databases, front-end computing-devices, servers and the like) shown as distinct for purposes of illustration may be incorporated within other functional elements, separated in different hardware, or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

The invention claimed is:

1. A method of exchanging STD test results that improves privacy-protection by allowing users to input requirements to allow the exchange of STD test results, the method comprising:

importing STD test results and identification information of an individual user;

importing business and business identification information of an establishment user;

the user selecting presets for STD-related criteria and minimum requirements for the exchange of STD test results to occur;

the user manually inputting user-definable criteria and minimum requirements;

the establishment user inputting user-definable criteria and minimum requirements;

utilizing STD test results and user identification stored in a database to generate a default and alternate STD criteria presets for matching the user to other users with: the same STD, lack of STD, less STD, or more STD;

estimating and displaying to the user the percentage of sexually-active people in an arbitrarily-defined or user-defined location and radius that meet the default and alternate STD criteria presets generated at default or user-definable permutations of levels of prevalence and undesirability of risking transmission on scales of 1-5;

specifying, by the user, individual STD that he tests positive or negative for and which he would not require other users to also test positive or negative for in order for the minimum requirement for the exchange of STD test results to occur to be met;

inputting user verification information required for attempting the exchange of STD test results and other functions such logging in or viewing the user's sexual contact history;

specifying, by the user, user verification methods required of other users for the attempt to exchange STD test results to occur;

specifying, by the user, what user verification methods specifiable by other users are required to be specified for the exchange of STD test results to occur with them;

specifying, by the user, whether manual viewing is required for the exchange of STD test results to occur if all involved parties meet each other's minimum requirements;

displaying to the user and specifying, by the user, his preferred presets for prevalence and undesirability of risking transmission by means of selecting maximum thresholds of allowable STD based upon the STD arbitrarily-defined prevalence or undesirability of risking transmission on scales of 1-5;

specifying, by the user, to attempt to exchange STD test results with other users;

displaying percentages of criteria met after adjusting for criterion weight functions during the attempt to exchange of STD test results if all involved parties meet the other users' minimum requirements;

displaying STD test results only if all users allow the exchange of STD test results after being shown the percentages of criteria met;

specifying, by the user, the requirements for updating other users she has exchanged STD test results with her most current STD test results as they become available;

storing the first and any additional combinations of selections under different "user profiles" in a database to allow the user to easily switch between different settings;

specifying, by the user, whether or not one-way exchanges of STD test results will be allowed for establishments, such as brothels, sex clubs, or HIV clubs;

specifying, by the user, the user to be automatically matched to other users who also wish to be automatically matched to other users utilizing inputted criteria, either at specific times or continuously, by performing a search for other users on a social media website or attempting to find other users within the vicinity of a small radius such as a sex club;

specifying, by the user, to provide payment information, for such uses as purchasing sexual health-related products and services or paying one-time fees or recurring fees for entrance to, membership to, or services of the establishment user; and specifying, by the establishment user, to provide bank routing number to offer and collect one-time payment or subscription payment options after the exchange of STD test results;

thereby improving the privacy-protection of the exchange of STD test results.

2. The method of claim 1, wherein the step of importing STD test results and identification information of the user comprises:

the user filling out an HIPAA form authorizing the release of STD test results;

the user providing additional user identification information in addition to what is required for STD testing to the STD center for future user verification uses;

requesting the release of the user's STD test results and user identification information from the STD center according to HIPAA guidelines; and storing the STD test results and identification information of the user in a database of a back-end computing-device.

3. The method of claim 1, wherein the step of importing business and business identification information of the establishment user comprises:

selecting type of establishment and services;

adding individuals who act as either users of the establishment account and authorizing their computing-devices;

inputting permitting and licensing information;

inputting establishment address and description; and storing the inputted information in a database of a back-end computing-device.

4. The method of claim 1, wherein the step of the user manually inputting user-definable criteria and minimum requirements for the exchange of STD test results to occur comprise of one or more of the following, in no specific order, and at the option of the user:

selecting presets for STD-related criteria and minimum requirements for the exchange of STD test results to occur for use as a template for manually-inputting user-definable criteria and minimum requirements for the exchange of STD test results to occur;

customizing STD-related and non-STD-related criteria, criterion weight functions, and minimum requirement for the exchange of STD test results to occur as a percentage;

using STD-related and/or non-STD-related criteria, criterion weight functions, and minimum requirement percentages in reference to the user himself as opposed to in reference to others;

creating custom STD-related and/or non-STD-related criteria and criterion weight functions;

separating STD-related and non-STD-related minimum requirement percentages when determining whether minimum requirements have been met;

specifying, by the user, to use the default or user-specified location and radius and displaying the estimated percentages of other sexually-active persons in the specified location and radius who match each specific criterion, STD-related criterion minimum requirement, non-STD-related criterion minimum requirement, and combined STD-related and non-STD-related criterion minimum requirement;

specifying, by the user, to be given the option to accept being marked as being granted entrance or membership to an establishment up to a specified date or duration, with such marking being usable either as a criterion during attempts to exchange STD test results and/or as a logo of the establishment displayable during manual user verification;

storing inputted preset and/or user-defined criteria, weight functions, minimum requirements, user identification information, and cryptographic hash code and hash code function for verifying the authenticity of the profile settings in a database of a back-end computing device; and encrypting and storing inputted preset and/or user-defined criteria, weight functions, minimum requirements, user identification information, and hash code and hash code function for verifying the authenticity of the user's and other users' profile settings in a memory of a front-end computing device belonging to the user to allow for the exchange of STD test results without internet communication to a back-end computing device.

5. The method of claim 1, wherein the step of the establishment user inputting user-definable criteria and minimum requirements for the one-way exchange of STD test results comprises:

specifying, by the user, allowable, unallowable, and required STD;

customizing STD-related and non-STD-related criteria, criterion weight functions, and minimum requirement for the exchange of STD test results to occur in reference to other users and also in reference to the establishment;

creating custom STD-related and/or non-STD-related criteria and criterion weight functions;

inputting user verification information required for attempting the exchange of STD test results and/or other functions such as viewing the user's sexual contact history;

specifying, by the user, user verification methods required of other users for the attempt to exchange STD test results to occur;

specifying, by the user, what user verification methods of other users are required to be used for the exchange of STD test results to occur;

specifying, by the user, whether manual viewing is required for the exchange of STD test results to occur if all involved parties meet each other's minimum requirements; and specifying, by the user, specific users for permanent, one-time, or temporary: blacklisting; entrance to the establishment; and/or access to the establishment services;

specifying, by the user, to either automatically or manually charge one-time or recurring fees for entrance to, membership, or services of the establishment or services of the establishment user after a successful one-way exchange of STD test results; and specifying, by the user, the option to mark users who allow such marking as having been granted entrance or membership to the establishment up to a specified date or duration;

storing inputted preset and/or user-defined criteria, weight functions, minimum requirements, user identification information, and cryptographic hash code and hash code function for verifying the authenticity of the profile settings in a database of a back-end computing device; and encrypting and storing inputted preset and/or user-defined criteria, weight functions, minimum requirements, user identification information, and hash code and hash code function for verifying the authenticity of the user's and other users' profile settings in a memory of a front-end computing device belonging to the user to allow for the exchange of STD test results without internet communication to a back-end computing device;

thereby the establishment user inputs user-definable criteria and minimum requirements for the one-way exchange of STD test results.

6. The method of claim 1, wherein the step of the user attempting to exchange STD test results with other users comprises:

the involved parties utilizing computing-devices such as cellular phones and computers to initiate an attempt to exchange STD test with each other either by: direct wireless communication between front-end computing-devices; and/or indirect communication between front-end computing-devices via internet communication between front-end and back-end computing-devices;

verifying the authenticity of all involved parties' profile settings if required by user settings and direct wireless communication between front-end computing-devices is allowed for the exchange of STD test results according to user settings;

verifying or verifying again the authenticity of all involved parties' profile settings if indirect communication between front-end computing-devices via internet communication between front-end and back-end computing-devices is allowed;

automatically verifying user identification information that are required by one or more involved parties for the attempt to exchange STD test results to occur;

displaying any required manually-verifiable user verification information of each involved party to all other involved parties attempting to exchange STD test results;

displaying "insufficient user verification information" if one or more parties lacks any of the user verification methods required by one or more parties for the attempt to exchange STD test results to occur;

denying the attempt to exchange STD test results if the attempt to automatically verify user identification information has failed to verify one or more of the required user identification information;

displaying "automatic user verification failed" if the attempt to automatically verify user identification information has failed to verify one or more of the required user identification information;

specifying, by all involved users, to allow or deny the attempt to exchange STD test results after viewing manually-verifiable user verification information;

denying the attempt to exchange STD test results if one or more of the involved parties has declined the attempt to exchange STD test results during the attempt to manually verify user identification information;

comparing the STD test results and criteria of the users stored in a memory of their front-end computing-devices if all involved parties have viewed user verification information, allow for the attempt to exchange STD test results, and allow for "offline" exchange of STD test results;

comparing the STD test results and criteria of the users stored in a database of a back-end computing-device if all involved parties have viewed user verification information, allow for the attempt to exchange STD test results, and require "online" exchange of STD test results;

determining the criteria that each user has met of other users' requirements for the exchange of STD test results to occur;

applying criterion weight functions to the criteria that each user has met of other users' requirements for the exchange of STD test results to occur; and determining the percentages of criteria that users have met of each of the other involved parties' requirements after adjusting for criterion weight functions.

7. The method of claim 1, wherein the step of displaying percentages of criteria met after adjusting for criterion weight functions if all involved parties meet all users' minimum requirements comprises:

determining whether or not the percentage of criteria that users have met of each of the other involved parties' requirements meet the minimum requirements for the exchange of STD test results to occur after adjusting for criterion weight functions;

preventing the exchange of STD test results if said minimum requirements are not met;

obscuring the cause of the prevention of the exchange of the STD test results by: the deliberate inclusion of non-STD-related criteria; and only displaying "Not a match" if the exchange of STD test results are prevented; and displaying said percentages of criteria met if said minimum requirements are met.

8. The method of claim 1, wherein displaying STD test results only if all users of the involved party allow the exchange of STD test results comprises:

displaying said percentages of criteria met to users requiring percentages of criteria met to be manually-viewed and confirmed for the exchange of STD test results to occur;

specifying, by users to automatically or manually allow or deny the exchange of STD test results after displaying said percentages of criteria met;

preventing the exchange of STD test results if one or more involved parties denies the exchange of STD test results;

preventing the exchange of STD test results if an arbitrarily-defined duration has passed without all parties specifying, by the user, the exchange of STD test results;

specifying, by the user, the exchange of STD test results if all involved parties allows the exchange of STD test results; and specifying, by the establishment user the option to automatically or manually offer one-time or recurring fees for entrance to, membership to, or services of the establishment to the individual user after a successful exchange of STD test results.

9. A system of exchanging STD test results that improves privacy-protection by allowing users to input requirements to allow the exchange of STD test results, the method comprising:

a front-end computing-device comprised of:
  memory;
  a display;
  a user interface;
  hardware internet communication between itself and a back-end computing device; and
  wireless communication between computing devices;
  computing devices for operating software implementing;

the back-end computing-device comprised of:
  memory;
  a user interface; and
  hardware internet communication between itself and front-end;
  wireless communication between computing devices;
  computing devices for operating software implementing;

importing STD test results and identification information of an individual user;

importing business and business identification information of an establishment user;

the user selecting presets for STD-related criteria and minimum requirements for the exchange of STD test results to occur;

the user manually inputting user-definable criteria and minimum requirements;

the establishment user inputting user-definable criteria and minimum requirements;

utilizing STD test results and user identification stored in a database to generate a default and alternate STD criteria presets for matching the user to other users with: the same STD, lack of STD, less STD, or more STD;

estimating and displaying to the user the percentage of sexually-active people in an arbitrarily-defined or user-defined location and radius that meet the default and alternate STD criteria presets generated at default or user-definable permutations of levels of prevalence and undesirability of risking transmission on scales of 1-5;

specifying, by the user, to specify individual STD that he tests positive or negative for and which he would not require other users to also test positive or negative for in order for the minimum requirement for the exchange of STD test results to occur to be met;

inputting user verification information required for attempting the exchange of STD test results and other functions such logging in or viewing the user's sexual contact history;

specifying, by the user, user verification methods required of other users for the attempt to exchange STD test results to occur;

specifying, by the user, what user verification methods specifiable by other users are required to be specified for the exchange of STD test results to occur with them;

specifying, by the user, whether manual viewing is required for the exchange of STD test results to occur if all involved parties meet each other's minimum requirements;

displaying to the user and specifying, by the user, his preferred presets for prevalence and undesirability of risking transmission by means of selecting maximum thresholds of allowable STD based upon the STD arbitrarily-defined prevalence or undesirability of risking transmission on scales of 1-5;

specifying, by the user, an attempt to exchange STD test results with other users;

displaying percentages of criteria met after adjusting for criterion weight functions during the attempt to exchange of STD test results if all involved parties meet the other users' minimum requirements;

displaying STD test results only if all users of the involved party allow the exchange of STD test results after being shown the percentages of criteria met;

specifying, by the user, the requirements for updating other users she has exchanged STD test results with her most current STD test results as they become available;

storing the first and any additional combinations of selections under different "user profiles" in a database to allow the user to easily switch between different settings;

specifying, by the user, whether or not one-way exchanges of STD test results will be allowed for establishments, such as brothels, sex clubs, or HIV clubs;

specifying, by the user, to be automatically matched to other users who also wish to be automatically matched to other users utilizing inputted criteria, either at specific times or continuously, performing a search for other users on a social media website or attempting to find other users within the vicinity of a small radius such as a sex club;

specifying, by the user, to provide payment information, for such uses as purchasing sexual health-related products and services or paying one-time fees or recurring fees for entrance to, membership to, or services of the establishment user; and specifying, by the establishment user, to provide bank routing number to offer and collect one-time payment or subscription payment options after the exchange of STD test results;

thereby improving the privacy-protection of the exchange of STD test results.

10. The system of claim 9, wherein the step of importing STD test results and identification information of the user comprises:

the user filling out an HIPAA form authorizing the release of STD test results;

the user providing additional user identification information in addition to what is required for STD testing to the STD center for future user verification uses;

requesting the release of the user's STD test results and user identification information from the STD center according to HIPAA guidelines; and storing the STD test results and identification information of the user in a database of a back-end computing-device.

11. The system of claim 9, wherein the step of importing business and business identification information of the establishment user comprises:

selecting type of establishment and services;

adding individuals who act as either users of the establishment account and authorizing their computing-devices;

inputting permitting and licensing information;

inputting the establishment address and description; and storing the inputted information in a database of a back-end computing-device.

12. The system of claim 9, wherein the step of the user manually inputting user-definable criteria and minimum requirements for the exchange of STD test results to occur comprise of one or more of the following, in no specific order, and at the option of the user:

selecting presets for STD-related criteria and minimum requirements for the exchange of STD test results to occur for use as a template for manually-inputting user-definable criteria and minimum requirements for the exchange of STD test results to occur;

customizing STD-related and non-STD-related criteria, criterion weight functions, and minimum requirement for the exchange of STD test results to occur as a percentage;

using STD-related and/or non-STD-related criteria, criterion weight functions, and minimum requirement percentages in reference to the user himself as opposed to in reference to others;

creating custom STD-related and/or non-STD-related criteria and criterion weight functions;

separating STD-related and non-STD-related minimum requirement percentages when determining whether minimum requirements have been met;

specifying, by the user, to use the default or user-specified location and radius and displaying the estimated percentages of other sexually-active persons in the specified location and radius who match each specific criterion, STD-related criterion minimum requirement, non-STD-related criterion minimum requirement, and combined STD-related and non-STD-related criterion minimum requirement;

specifying, by the user, the option to accept being marked as being granted entrance or membership to an establishment up to a specified date or duration, with such marking being usable either as a criterion during attempts to exchange STD test results and/or as a logo of the establishment displayable during manual user verification;

storing inputted preset and/or user-defined criteria, weight functions, minimum requirements, user identification information, and cryptographic hash code and hash code function for verifying the authenticity of the profile settings in a database of a back-end computing device; and encrypting and storing inputted preset and/or user-defined criteria, weight functions, minimum requirements, user identification information, and hash code and hash code function for verifying the authenticity of the user's and other users' profile settings in the memory of a front-end computing device belonging to the user to allow for the exchange of STD test results without internet communication to a back-end computing device.

13. The system of claim 9, wherein the step of the establishment user inputting user-definable criteria and minimum requirements for the one-way exchange of STD test results comprises:

specifying, by the user, allowable, unallowable, and required STD;

customizing STD-related and non-STD-related criteria, criterion weight functions, and minimum requirement for the exchange of STD test results to occur in reference to other users and also in reference to the establishment;

creating custom STD-related and/or non-STD-related criteria and criterion weight functions;

inputting user verification information required for attempting the exchange of STD test results and/or other functions such as viewing the user's sexual contact history;

specifying, by the user, user verification methods required of other users for the attempt to exchange STD test results to occur;

specifying, by the user, what user verification methods of other users are required to be used for the exchange of STD test results to occur;

specifying, by the user, whether manual viewing is required for the exchange of STD test results to occur if all involved parties meet each other's minimum requirements; and specifying, by the user, specific users for permanent, one-time, or temporary: blacklisting; entrance to the establishment; and/or access to the establishment services;

specifying, by the user, to either automatically or manually charge one-time or recurring fees for entrance to, membership, or services of the establishment or services of the establishment user after a successful one-way exchange of STD test results; and specifying, by the user, the option to mark users who allow such marking as having been granted entrance or membership to the establishment up to a specified date or duration;

storing inputted preset and/or user-defined criteria, weight functions, minimum requirements, user identification information, and cryptographic hash code and hash code function for verifying the authenticity of the profile settings in a database of a back-end computing device; and encrypting and storing inputted preset and/or user-defined criteria, weight functions, minimum requirements, user identification information, and hash code and hash code function for verifying the authenticity of the user's and other users' profile settings in the memory of a front-end computing device belonging to the user to allow for the exchange of STD test results without internet communication to a back-end computing device;

thereby the establishment user inputs user-definable criteria and minimum requirements for the one-way exchange of STD test results.

14. The system of claim 9, wherein the step of the user attempting to exchange STD test results with other users comprises:

the involved parties utilizing computing-devices such as cellular phones and computers to initiate an attempt to exchange STD test with each other either by: direct wireless communication between front-end computing-devices; and/or indirect communication between front-end computing-devices via internet communication between front-end and back-end computing-devices;

verifying the authenticity of all involved parties' profile settings if required by user settings and direct wireless communication between front-end computing-devices is allowed for the exchange of STD test results according to user settings;

verifying or verifying again the authenticity of all involved parties' profile settings if indirect communication between front-end computing-devices via internet communication between front-end and back-end computing-devices is allowed;

automatically verifying user identification information, that are required by one or more involved parties for the attempt to exchange STD test results to occur;

displaying any required manually-verifiable user verification information of each involved party to all other involved parties attempting to exchange STD test results;

displaying "insufficient user verification information" if one or more parties lacks any of the user verification methods required by one or more parties for the attempt to exchange STD test results to occur;

denying the attempt to exchange STD test results if the attempt to automatically verify user identification information has failed to verify one or more of the required user identification information;

displaying "automatic user verification failed" if the attempt to automatically verify user identification information has failed to verify one or more of the required user identification information;

specifying, by the user, to allow or deny the attempt to exchange STD test results after viewing manually-verifiable user verification information;

denying the attempt to exchange STD test results if one or more of the involved parties has declined the attempt to exchange STD test results during the attempt to manually verify user identification information;

comparing the STD test results and criteria of the users stored in the memory of their front-end computing-devices if all involved parties have viewed user verification information, allow for the attempt to exchange STD test results, and allow for "offline" exchange of STD test results;

comparing the STD test results and criteria of the users stored in a database of a back-end computing-device if all involved parties have viewed user verification information, allow for the attempt to exchange STD test results, and require "online" exchange of STD test results;

determining the criteria that each user has met of other users' requirements for the exchange of STD test results to occur;

applying criterion weight functions to the criteria that each user has met of other users' requirements for the exchange of STD test results to occur; and determining the percentages of criteria that users have met of each of the other involved parties' requirements after adjusting for criterion weight functions.

15. The system of claim 9, wherein the step of displaying percentages of criteria met after adjusting for criterion weight functions if all involved parties meet all users' minimum requirements comprises:

determining whether or not the percentage of criteria that users have met of each of the other involved parties' requirements meet the minimum requirements for the exchange of STD test results to occur after adjusting for criterion weight functions;

preventing the exchange of STD test results if said minimum requirements are not met;

obscuring the cause of the prevention of the exchange of the STD test results by: the deliberate inclusion of non-STD-related criteria; and only displaying "Not a match" if the exchange of STD test results are prevented; and displaying said percentages of criteria met if said minimum requirements are met.

16. The system of claim 9, wherein displaying STD test results only if all users of the involved party allow the exchange of STD test results comprises:

displaying said percentages of criteria met to users requiring percentages of criteria met to be manually-viewed and confirmed for the exchange of STD test results to occur;

specifying, by users, whether to automatically or manually allow or deny the exchange of STD test results after displaying said percentages of criteria met;

preventing the exchange of STD test results if one or more involved parties denies the exchange of STD test results;

preventing the exchange of STD test results if an arbitrarily-defined duration has passed without all parties specifying the exchange of STD test results;
specifying, by the user, the exchange of STD test results if all involved parties allows the exchange of STD test results; and
specifying, by the establishment user, the option to automatically or manually offer one-time or recurring fees for entrance to, membership to, or services of the establishment to the individual user after a successful exchange of STD test results.

17. A non-transitory computer readable medium comprising executable instruction that, when executed by a computing device configured to execute the exchange of STD test results in a manner that optimizes privacy-protection, the steps comprising:
    importing STD test results and identification information of the individual user;
    importing business and business identification information of the establishment user;
    the user selecting presets for STD-related criteria and minimum requirements for the exchange of STD test results to occur;
    the user manually inputting user-definable criteria and minimum requirements;
    the establishment user inputting user-definable criteria and minimum requirements;
    utilizing STD test results and user identification stored in a database to generate a default and alternate STD criteria presets for matching the user to other users with: the same STD, lack of STD, less STD, or more STD;
    estimating and displaying to the user the percentage of sexually-active people in an arbitrarily-defined or user-defined location and radius that meet the default and alternate STD criteria presets generated at default or user-definable permutations of levels of prevalence and undesirability of risking transmission on scales of 1-5;
    specifying, by the user, individual STD that he tests positive or negative for and which he would not require other users to also test positive or negative for in order for the minimum requirement for the exchange of STD test results to occur to be met;
    inputting user verification information required for attempting the exchange of STD test results and other functions such logging in or viewing the user's sexual contact history;
    specifying, by the user, user verification methods required of other users for the attempt to exchange STD test results to occur;
    specifying, by the user, what user verification methods specifiable by other users are required to be specified for the exchange of STD test results to occur with them;
    specifying, by the user, whether manual viewing is required for the exchange of STD test results to occur if all involved parties meet each other's minimum requirements;
    displaying to the user and specifying, by the user, his preferred presets for prevalence and undesirability of risking transmission by means of selecting maximum thresholds of allowable STD based upon the STD arbitrarily-defined prevalence or undesirability of risking transmission on scales of 1-5;
    specifying, by the user, an attempt to exchange STD test results with other users;
    displaying percentages of criteria met after adjusting for criterion weight functions during the attempt to exchange of STD test results if all involved parties meet the other users' minimum requirements;
    displaying STD test results only if all users of the involved party allow the exchange of STD test results after being shown the percentages of criteria met;
    specifying, by the user, the requirements for updating other users she has exchanged STD test results with her most current STD test results as they become available;
    storing the first and any additional combinations of selections under different "user profiles" in a database to allow the user to easily switch between different settings;
    specifying, by the user, whether or not one-way exchanges of STD test results will be allowed for establishments, such as brothels, sex clubs, or HIV clubs;
    specifying, by the user, to be automatically matched to other users who also wish to be automatically matched to other users utilizing inputted criteria, either at specific times or continuously, performing a search for other users on a social media website or attempting to find other users within the vicinity of a small radius such as a sex club;
    specifying, by the user, to provide payment information, for such uses as purchasing sexual health-related products and services or paying one-time fees or recurring fees for entrance to, membership to, or services of the establishment user; and
    specifying, by the establishment user, to provide bank routing number to offer and collect one-time payment or subscription payment options after the exchange of STD test results;
thereby improving the privacy-protection of the exchange of STD test results.

* * * * *